United States Patent [19]
Shuler

[11] Patent Number: 6,162,398
[45] Date of Patent: Dec. 19, 2000

[54] ASSAY DEVICE USING SHRINK WRAP

[75] Inventor: John K. Shuler, Baltimore, Md.

[73] Assignee: Becton Dickinson and Company, Franklin Lakes, N.J.

[21] Appl. No.: 09/060,879

[22] Filed: Apr. 16, 1998

[51] Int. Cl.[7] .......................... G01N 21/00; G01N 21/22; G01N 33/53; G01N 21/75; C12M 1/34
[52] U.S. Cl. .................. 422/58; 422/56; 422/58; 422/60; 422/61; 422/104; 436/518; 436/530; 436/161; 436/164; 436/169; 436/529; 436/805; 435/7.92; 435/7.93; 435/7.94; 435/810; 435/287.2; 435/287.7; 435/287.8; 435/287.9
[58] Field of Search ..................... 436/518, 530, 436/164, 161, 169, 529, 805; 435/7.92, 7.93, 7.94, 810, 287.2, 287.7, 287.8, 287.9; 422/56, 58, 60, 61, 104

[56] References Cited

U.S. PATENT DOCUMENTS

| | | |
|---|---|---|
| 3,916,914 | 11/1975 | Brooks et al. ................ 131/10 |
| 4,693,834 | 9/1987 | Hossom et al. ................ 210/767 |
| 5,559,041 | 9/1996 | Kang et al. ................ 436/529 |
| 5,728,587 | 3/1998 | Kang et al. ................ 436/518 |

FOREIGN PATENT DOCUMENTS 794508  1/1981  U.S.S.R. .

*Primary Examiner*—Long V. Le
*Assistant Examiner*—Gailene R. Gabel
*Attorney, Agent, or Firm*—Bruce S. Weintraub, Esq.

[57] ABSTRACT

Devices for conducting an assay are disclosed which utilize shrink wrap as a casing material. The use of shrink wrap casings enables the preliminary fluid filtering step and the chemical detection step to be combined, provides improved control over the flow of fluids into and through the assay device and reduces the time, material, effort, expense and risk of contamination involved in conducting assays.

32 Claims, 5 Drawing Sheets

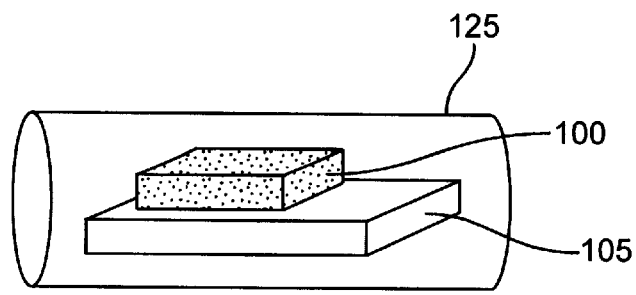
FIG. 7A
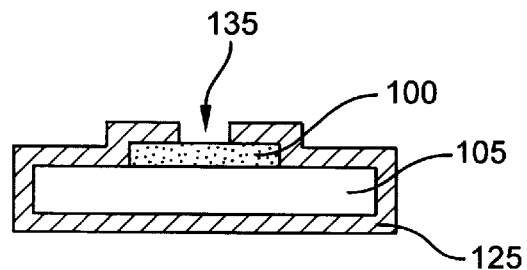
FIG. 7B
FIG. 8  PRIOR ART
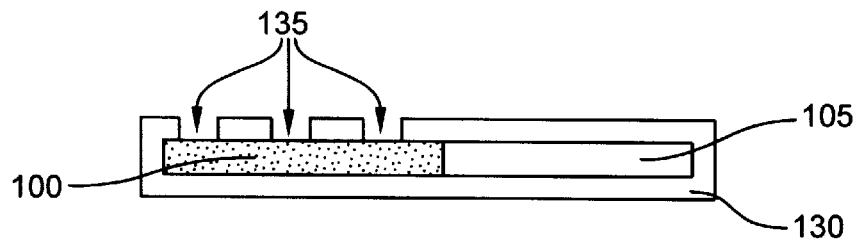
FIG. 9
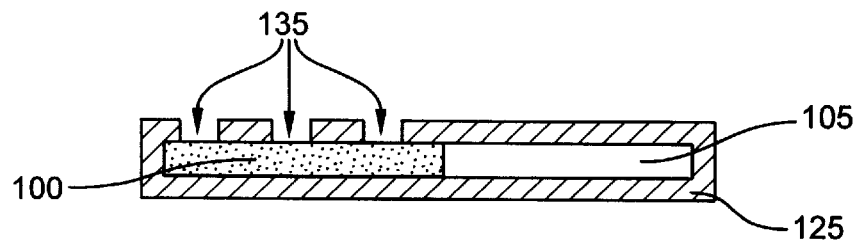

ASSAY DEVICE USING SHRINK WRAP

FIELD OF THE INVENTION

This invention relates to devices for conducting assays to determine whether materials of interest are present in biological and/or industrial fluids. More specifically, this invention relates to devices for conducting assays to detect and identify infection causing antigens in bodily fluids.

BACKGROUND OF THE INVENTION

Assay devices are utilized in a wide variety of fields, most notably medical diagnostics, to test for materials of interest, such as antigens from infection causing organisms. In the medical field, given the already large number of known infections, and the ever growing number of new infections, assay technology has become increasingly important.

For example, streptococci is an organism that can cause illnesses such as tonsillitis, pharyngitis, and scarlet fever. If left untreated, a strep infection can lead to numerous complications, such as rheumatic fever. Therefore, it is important to treat infections as quickly and effectively as possible.

However, before an infection can be treated the infection causing agent must be identified. Confirmation of the presence and identity of infective agents in a patient is best affected by diagnostic procedures that are usually multiple step processes comprising: (1) sampling a bodily fluid, e.g. blood, saliva, urine, etc . . . ; (2) filtering the fluid in order to better isolate any antigens present; (3) contacting the filtered fluid with a detection material that contains bound antibodies reactive with the antigens of interest so that the antigens of interest bind to the antibodies and, therefore, to the detection device; and (4) contacting the detection device with "detector" antibodies that are reactive with the antigens of interest and that also contain bound signal producing systems such as dyes. The antibodies and therefore, the dyes, attach to the bound antigens and, thereby, in the simpliest case, provide a visual marker signifying the presence and identity of the antigens.

The antibodies described in the forestated process are blood serum proteins that are formed by the body as a natural part of its response to the introduction of an antigen. The entire science of immunology is based on antigen-antibody reactions, the most outstanding feature of which is their specificity. Antibodies in the bloodstream usually react only with the antigen used to stimulate their production or with antigens of a similar molecular structure. The specificity of antibodies towards antigens is due not so much to the composition of the molecules as it is to the configuration of the molecules.

In the prior art, multiple devices are necessary to perform the multiple step process of detecting and identifying antigens. In one such example, bodily fluid is drawn into a capillary tube. The bodily fluid is then dropped into a dispensing tube that contains a lysing reagent. A tip containing a sifting filter is then utilized to cover the tube opening. As used in this application, the term "sifting filter" means any material utilized to limit the size or nature of components present in a test fluid sample. The sifting filter, upon inversion of the dispensing tube, allows lysed fluid to pass out of the tube. The dispensing tube is then inverted and a drop of lysed fluid is placed into a well on a reaction stand.

Prior art assays generally comprise: (1) a "reservoir filter," defined herein as any filter that absorbs excess test fluid and increases the capillary action drawing the test fluid through the assay device; (2) a detection zone that is aligned contiguous to the reservoir filter, which comprises a detection zone base material, such as nitrocellulose, and a means for detecting the material of interest, in this case attached homologous antibodies reactive with the antigen of interest; and (3) a backing that supports both the reservoir filter and the detection zone. Optionally, a protective covering, usually plastic, can also be added that is bound to the backing and extends over the reservoir filter and/or the detection material to further bind the materials to the backing.

The prior art assays may be dipped into the lysed fluid so that the fluid enters the assay as close to the terminal point of the detection material as possible. Capillary action then sucks the fluid through the detection zone and into the reservoir filter. The attached antibodies in the detection zone then chemically and/or physically bind the antigens as they pass through the detection zone. Concurrently, or in a subsequent step, detector antibodies that contain bound dyes are contacted with the bound antigens. The antibodies that contain bound dyes attach to the bound antigens and provide a visual color marker that signifies the presence and identify of the antigens.

One problem with the prior art method is that multiple devices (capillary tube, dispensing tube, sifting filter tip, and assay) are necessary, or the process is cumbersome, time consuming and prone to contamination error. The practitioner needs to ensure the sterility and integrity of at least four different devices to avoid contamination.

In addition, there is no mechanism in the prior art assays that controls the test fluid in a manner sufficient to ensure that it only enters the assay at the terminus of the detection zone. This is critical for optimal performance of the system since antigens contained in fluid entering the sides of the detection zone may miss many of the bounded antibodies and, therefore, never be detected. Although hard plastic casings presumably offer a modicum of control over the flow of test fluids and are known for use in assays, these casings are less efficient, bulky and expensive.

In response to long felt needs in the industry, and in an effort to rectify the problems inherent in the prior art devices for detecting and identifying antigens, applicants have designed an improved device for conducting assays.

The device disclosed within this application performs both the sifting filter process and the assay process, thereby cutting time, effort, and the risk of contamination. The inventive device utilizes shrink wrap technology to encase the sifting filter contiguous to the assay test strip. However, the shrink wrap does more than simply serve as a encasing agent. The shrink wrap also directs the test fluid in a manner that ensures that it only enters the assay through the terminus of the sifting filter and, subsequently, the terminus of the detection zone. As stated, this is critical for a working system.

Furthermore, the device disclosed within this application may be identical to any one of several conventional assays but, instead of being encased in a hard plastic, it is encased in shrink wrap.

The phrase "shrink wrap," as used in this application, is defined as a plastic film that reduces in size upon application of heat. Shrink wrap is an ideal encasing material since it is both cheap to produce and easily integrated into mass production assemblies. As a result, the use of shrink wrap to produce an improved assay adds minimal cost to assay production. This cost advantage cannot be overstated. Although assays are universally utilized in the medical industry to test for an already enormous, and ever expanding, number of infections, the large demand for assays is countered by an even larger aversion to increased health care costs. Therefore, any improvement in the assay art that is significantly more expensive is not readily accepted. In contrast, the traditional hard plastic casings are very expensive.

In addition, shrink wrap provides a tighter casing around the assay than can be obtained with the traditional hard plastic casings. As a result, shrink wrap is more effective in directing the test fluid so that it only enters the assay through the terminus of the detection zone.

Finally, unlike the traditional hard plastic casings, shrink wrap provides a very thin casing which makes handling and storage easier.

Although the inventive assay device is primarily geared toward detecting and identifying infection causing antigens in bodily fluids, it should be recognized, and is certainly envisioned, that the assay device is capable of detecting and identifying any material of interest in any biological and/or industrial fluid, as long as the detection zone contains a means of chemically, and/or physically, trapping, and/or tagging, the material of interest. The nature of the means of trapping and/or tagging the material of interest will naturally vary according to the nature of the material of interest and is readily ascertainable by those of ordinary skill in the art. For example, if the material of interest is a DNA, the means of trapping and/or tagging the material of interest is a complementary DNA and, if the material of interest is an PNA (Peptide Nucleic Acid), the means for trapping and/or tagging the material of interest is a complementary PNA. An infinite number of compounds can be detected in biological and/or industrial fluids utilizing the inventive assays, including, but not limited to, analytes, antigens, polynucleotides, oligonucleotides, small molecules, drugs of abuse, therapeutic drugs, carbohydrates, environmental and carcinogenic agents, parasites, bacteria, viruses, and prions.

SUMMARY OF THE INVENTION

The invention is to several new devices for conducting an assay to determine whether materials of interest, notably antigens, are present in biological and/or industrial fluids, notably bodily fluids.

In a first inventive embodiment, the device for conducting an assay comprises: (a) a detection zone, wherein the detection zone comprises (i) a detection zone material that permits the passage of fluid via capillary action and (ii) a means for chemically, and/or physically, trapping and/or tagging, at least one material of interest contained in said fluid wherein said means can be a binder; (b) a sifting filter containing one inlet, wherein the sifting filter permits the passage of fluid via capillary action, and, further, wherein the sifting filter is aligned contiguous to the detection material; optionally, (c) a reservoir zone aligned contiguous to the detection material and located on the side opposite the sifting filter, wherein the reservoir zone absorbs fluid via capillary action; optionally, (d) an underlying backing material that provides support for the detection zone and/or the sifting filter and/or the reservoir zone; (e) a casing material comprising a shrink wrap material, wherein the casing material is applied circumferentially around at least the boundary of the one inlet of the sifting filter and any underlying backing in a manner that does not close the inlet; and, optionally, (f) a covering material. FIGS. 3, 4A, 4B and 4C are illustrative of this first embodiment.

This first inventive assay device is an advancement over prior art assay devices for a number of reasons. First, the placement of a sifting filter immediately preceding the detection zone eliminates the necessity of filtering blood in a dispenser tube. Therefore, the extra expense of a dispenser tube filter tip and a dispenser are eliminated. This results in a more cost effective testing system, reduces complexity of the testing procedure, reduces volume of the specimen and lysing solution required, and lowers the risk of cross-contamination.

Second, this first inventive assay device is cheaper and easier to manufacture, handle, and store, than systems in the prior art because expensive accessories are eliminated.

Third, the shrink wrap used in this first inventive assay device not only serves as an effective structural support for the assay components, but also directs the flow of the test fluid in a manner superior to hard plastic casings due to the form fitting nature of shrink wrap. The shrink wrap controls the test fluid flow so that the test fluid only enters the device through the filter inlet and, therefore, only enters the detection zone at its terminus. Only the inlet is exposed to the testing sample. Thus, the shrink wrap acts as a flow restrictor to channel the fluid sample into the inlet of the assay.

In a second inventive embodiment, the device for conducting an assay comprises: (a) a detection zone containing one inlet, wherein the detection zone comprises (i) a detection zone material that permits the passage of fluid via capillary action and (ii) a means for chemically, and/or physically, trapping and/or tagging, at least one material of interest contained in said fluid; optionally, (b) a reservoir zone aligned contiguous to the detection material, wherein the reservoir zone absorbs fluid via capillary action; optionally, (c) an underlying backing material that provides support for the detection zone and/or the sifting filter and/or the reservoir zone; (d) a casing material comprising a shrink wrap material, wherein the casing material is applied circumferentially around at least the boundary of the one inlet of the sifting material and any underlying backing in a manner that does not close the inlet; and, optionally, (e) a covering material.

Once again, this assay device is cheaper and easier to manufacture, handle, and store than prior art assay devices. Furthermore, by tightly covering at least the boundary of the detection zone inlet, the shrink wrap directs the test fluid so that it only enters the detection zone at its terminus. When the backing is present, the shrink wrap effectively adheres the detection zone and the reservoir filter, if present, to the backing. An example of this second inventive assay utilizing a reservoir zone, is set forth in FIG. 5.

In a third embodiment, the device for conducting an assay comprises: (a) a detection zone comprising (i) a detection zone material that permits the passage of fluid via capillary action and (ii) a means for chemically, and/or physically, trapping and/or tagging, at least one material of interest contained in said fluid; (b) a reservoir zone located immediately below the detection zone that absorbs fluid via capillary action; (c) a casing material comprising a shrink wrap material, wherein said casing material completely surrounds the entire assay device; and (d) at least one inlet in the casing located immediately above the detection zone sufficient to add test fluids to the assay device.

In this embodiment, shrink wrap is employed to obtain a cheaper, tighter and thinner casing for the entire assay device relative to the conventional hard plastic casings utilized in identical prior art devices. Shrink wrap casings are made of cheaper materials and are more easily integrated into mass production assembly processes than traditional hard plastic casings and, therefore, produce a more cost effective casing.

The casing is more effective as a protective layer and test fluid guiding agent since it bonds tighter to the surface of the device than conventional hard plastic casings. Finally, the thinner casing obtained utilizing shrink wrap is easier to handle and store relative to conventional hard plastic casings. FIGS. 7A and 7B are illustrative of this embodiment.

In a fourth embodiment, the device for conducting an assay comprises: (a) a detection zone, wherein the detection zone comprises (i) a detection zone material that permits the passage of fluid via capillary action and (ii) a means for chemically, and/or physically, trapping and/or tagging, at least one material of interest contained in said fluid; (b) an optional sifting zone, wherein the sifting filter permits the passage of fluid via capillary action, and, further, wherein the sifting filter is aligned contiguous to the detection material; optionally, (c) a reservoir zone aligned contiguous to the detection material and located on the side opposite the sifting filter, if present, wherein the reservoir zone absorbs fluid via capillary action; optionally, (d) an underlying backing material that provides support for the detection zone and/or the sifting filter and/or reservoir zone; (e) a casing comprising a shrink wrap material, wherein said casing completely surrounds the entire assay device; and (f) at least two inlets in the casing wherein one of the inlets is for the addition of test fluids to the assay device and the other inlet is for the addition of reagents, such as lysing reagents, to the assay device. Other inlets may be present for purposes such as adding additional reagents and/or adding tagging chemicals and/or better clarity in visually reviewing the results. Preferably, the device also contains a reagent container that can be broken to release reagent, located in contact with the second inlet and surrounded by the shrink wrap casing, effectively affixing and sealing the reagent container and assuring that the released reagent stays sealed around the inlet when the reagent container is broken.

In this embodiment, shrink wrap is employed to obtain a cheaper, tighter and thinner casing for the entire assay device relative to the conventional hard plastic casings utilized in identical prior art devices. Shrink wrap casings are made of cheaper materials and are more easily integrated into mass production assembly processes than traditional hard plastic casings and, therefore, produce a more cost effective casing. The casing is more effective as a protective layer and test fluid guiding agent since it bonds tighter to the surface of the device than conventional hard plastic casings. Finally, the thinner casing obtained utilizing shrink wrap is easier to handle and store relative to conventional hard plastic casings. FIGS. 7A and 7B are illustrative of this embodiment. In addition, attaching a breakable reagent container by shrink wrap provides a more consolidated, effective, safe, and contaminate free method for adding reagent. FIG. 9 is illustrative of this embodiment utilizing a reservoir zone and backing, but not a sifting filter or optional reagent container.

BRIEF DESCRIPTION OF THE DRAWINGS

FIGS. 7A and 7B illustrate a third embodiment of the present inventive assay device.

FIG. 8 shows an assay device used in the prior art.

FIG. 9 illustrates a fourth embodiment of the present inventive assay device.

DESCRIPTION OF THE PREFERRED EMBODIMENT(S)

I. First Inventive Assay Device

Figure 1A:
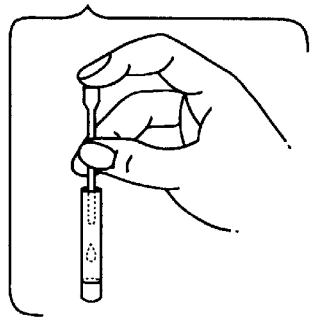
FIGS. 1A, 1B, 1C, 1D and 1E show the most common assay method in the prior art.
Figure 1B:
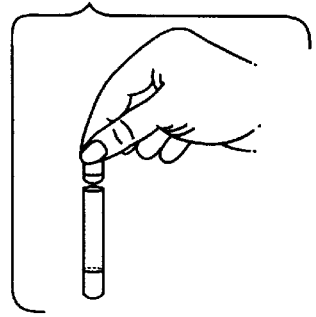
Figure 1C:
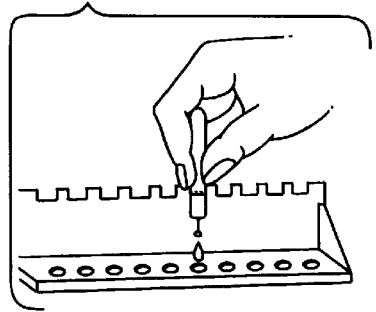
Figure 1D:
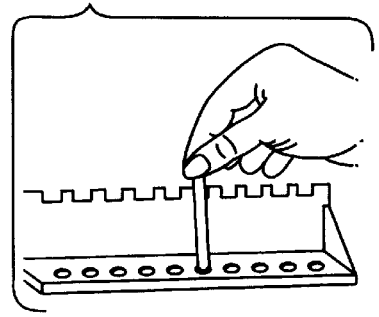
Figure 1E:
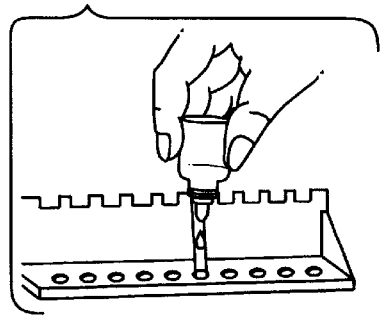

FIGS. 1A, 1B, 1C, 1D and 1E show the most common assay method in the prior art. First, as shown in FIG. 1A, blood from a capillary tube is placed into a dispensing tube containing a red blood cell lysing solution. Next, as shown in FIG. 1B, a tip is placed onto the dispensing tube. The tip contains a sifting filter which allows lysed whole blood to be dispensed from the dispensing tube once the tube is inverted. As shown in FIG. 1C, the dispensing tube is then inverted and a drop of lysed blood is placed into a well on a reaction stand. Finally, an assay device is placed into contact with the dispensed lysed blood in the well of the reaction stand, as shown in FIG. 1D. The assay may rest against a portion of the reaction stand, in order to prevent the assay from falling over. Optionally, as shown in FIG. 1E, reagents or other reactive chemicals may be added to the well in order to process the sample.

Figure 2:
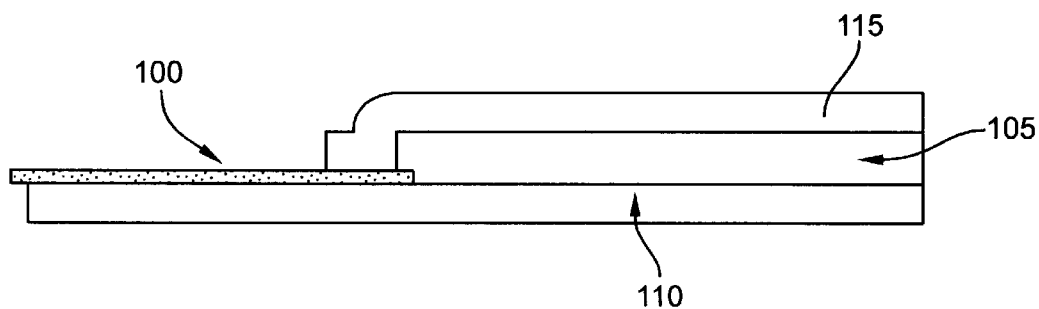
FIG. 2 shows a cross section of the a prior art assay device used in the assay method set forth in FIG. 1.

FIG. 2 shows a cross section of the prior art assay utilized in FIG. 1. As shown in FIG. 2, the assay comprises a detection zone (100) containing a detecting means. The detection zone (100) is located adjacent to a reservoir filter (105). The detection zone (100) and reservoir filter (105) are each disposed upon a backing material (110). A covering material (115) may be placed over the detection zone (100) and the reservoir filter (105) to hold the reservoir filter (105) onto the backing material (110) and the detection zone (100). In use, blood or other samples are placed on the detection zone (100). Capillary action draws the fluid sample through the detection zone (100) and into the reservoir filter (105). Reagents or other materials may be contacted to the detection zone (100) and also flow by capillary action through the detection zone (100) and into the reservoir filter (105).

Applicants have developed a substantial improvement over this prior art assay that utilizes shrink wrap as an outer covering.

The new device for conducting an assay comprises: (a) a detection zone, wherein the detection zone comprises (i) a detection zone material that permits the passage of fluid via capillary action and (ii) a means for chemically, and/or physically, trapping and/or tagging, at least one material of interest contained in said fluid; (b) a sifting filter containing one inlet, wherein the sifting filter permits the passage of fluid via capillary action, and, further, wherein the sifting filter is aligned contiguous to the detection material; optionally, (c) a reservoir zone aligned contiguous to the detection material and located on the side opposite the sifting filter, wherein the reservoir zone absorbs fluid via capillary action; optionally, (d) an underlying backing material that provides support for the detection zone and/or the sifting filter and/or the reservoir zone; (e) a casing material comprising a shrink wrap material, wherein the casing material is applied circumferentially around at least the boundary of the one inlet of the sifting material, and any underlying backing, in a manner that does not close the inlet; and, optionally, (f) a covering material. Preferably, the device for conducting an assay comprises: (a) said detection zone; (b) said sifting filter; (c) said reservoir zone; and (e) said casing material. Most preferably, the device for conducting an assay comprises: (a) said detection zone; (b) said sifting filter; (c) said reservoir zone; (d) said backing; and (e) said casing material.

The optional backing material is any material that adds structural support. To add structural support the backing material must have a greater rigidity than the sifting filter, detection zone, and the reservoir zone. In addition, the backing material should be nonabsorbent. Absorbent materials create capillary actions that compete with the capillary action caused by the reservoir filter and, thereby, undermine the effective functioning of the assay. Preferred backing materials include mylar, polyester, and vinylchloride polymers and copolymers. The most preferred backing material is a polyester laminate with an adhesive coating.

The detection zone material must be a material that allows fluid to pass through it via capillary action. In addition, the detection zone material must be a material capable of being modified to contain a means for chemically and/or physically trapping and/or tagging a material of interest. Suitable detection zone materials have a defined pore size structure wherein the pore size is about 0.1 to 20 microns. Preferred detection zone materials include glass fiber, cellulose, nylons such as Pall's BIODYNE C, crosslinked dextran, various chromatographic papers, and nitrocellulose. The most preferred detection zone material is a nitrocellulose membrane.

The term "sifting filter," as used in this application, means any material utilized to limit the size or nature of components present in a test fluid sample. The sifting filter may be any material that allows fluid to pass via capillary action. Preferred sifting filter materials include glass fiber, cellulose, and nylon. The most preferred sifting filter materials is Gelman glass fiber type A/B.

The sifting filter may contain a number of reagents. One such reagent is a lysing reagent. Lysing reagents cause the dissolution and/or destruction of cells. Preferred lysing agents are surfactants. The most preferred lysing agents are zwitterionic detergents.

The term "reservoir zone," as used in this application, is defined as being comprised of a reservoir material that absorbs excess test fluid and increases the capillary action drawing the test fluid through the assay. The reservoir material is chosen from the same materials set forth in the preceding description of the sifting filter, namely, any material that allows fluid to pass via capillary action, preferably glass fiber, cellulose, and nylon, most preferably nylon and Gelman glass fiber type A/B.

The casing material comprises shrink wrap and is preferably made up primarily of shrink wrap, and is most preferably made up entirely of shrink wrap. The phrase "shrink wrap," as used in this application, is defined as a plastic film, or blend of plastic films, that reduces in size upon the application of heat. Suitable shrink wrap materials are chosen from the group consisting of shrinkable flexible thermoplastic films. Preferred shink wrap materials include linear or branched, high medium or low density, polyolefins wherein the term polyolefin includes polyethylene, polypropylene, ethylene-propylene copolymers, and ethylene copolymers made using comonomers such as vinyl chloride. The most preferred shrink wrap materials are chosen from the group consisting of linear or branched, high, medium or low density, polyethylene. The casing comprising shrink wrap is created by applying a tube of shrink wrap around the objects to be encased and then heating the tube at a temperature of at least 70° C. for approximately one minute so that the shrink wrap tightens around the objects to create a form fitting casing.

The optional covering material is a means of further binding the detection zone, and optional reservoir filter to the backing material. The optional covering material is not particularly limited. Preferred covering materials are polymeric, paper and paper/polymer laminates. The most preferred covering material is a paper laminate with an adhesive coating.

The binder, or means of chemically and/or physically trapping and/or tagging at least one material of interest present in the test fluid naturally varies with the nature of the material of interest and is readily ascertainable by those of ordinary skill in the art. For example, if the material of interest (analyte) is an infection causing antigen contained within a bodily fluid such as blood, saliva or urine, the binder, or means of trapping and/or tagging the material of interest is an antibody homologous to the antigen. In further example, if the material of interest is a DNA, the means of trapping and/or tagging the material of interest is a complementary DNA and if the material of interest is a PNA, the means for trapping and/or tagging the material of interest is a complementary PNA.

Since antigens are the most common material of interest, the means for trapping and/or tagging the material of interest is generally an antibody. Antibodies are blood serum proteins that are formed by the body as a natural part of its response to the introduction of an antigen. Antibodies produced in the bloodstream can react only with homologous antigens or with antigens of a similar molecular structure. The specificity of antigens is due not so much to the composition of the molecules as it is to the configuration of the molecules.

When the assay device is utilized to detect antigens from disease causing organisms, antibodies specific to the antigens are present in the detection zone material either as free unattached compounds or as compounds bound to the detection zone material. It is preferred, however, that the antibodies be bound to the detection zone material. As the test fluid passes through the detection zone material, driven by capillary action, the antigens attach to the antibodies attached to the detection zone material and become fixed in place within the detection zone.

Antibody coated liposomes containing a colored dye are then utilized to visually mark the presence of the antigen in the detection zone. The antibody coated liposomes containing a colored dye are an example of a "tagging agents." These tagging agents can be added to the sifting filter and/or the detection zone during the assembly of the assay device. Alternatively, these tagging agents can be added immediately prior to, or immediately subsequent to, the addition of the test fluid to the assay device via the same method utilized to introduce the test fluid to the assay device. The antibody coated liposomes attach to the antigens bound to the detection zone and the accompanying dye provides a visual marker signifying the presence and identity of the infection causing antigen.

Figure 3:
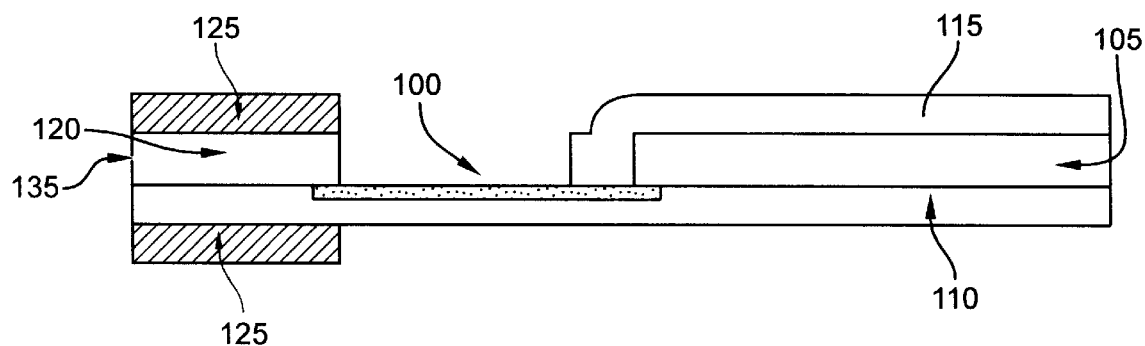
FIG. 3 illustrates a first embodiment of the present inventive assay device.

FIG. 3 is illustrative of this first embodiment of the present invention. As shown in FIG. 3, a detection zone (100), which may be a nitrocellulose membrane containing bound antibodies, is placed adjacent to a reservoir filter (105), and each material is then disposed atop a backing material (110). A covering (115) is placed over the detection zone (100) and the reservoir filter (105) to hold the reservoir filter (105) and the detection zone (100) onto the backing material (110). A sifting filter (120) is placed contiguous to detection zone (100) on the opposite side as the reservoir zone (105). A shrink wrap material (125) is then positioned around at least the sifting filter (120) and the underlying portion of the backing material (110). Upon the application of heat, the shrink wrap (125) will reduce in size and surround the sifting filter (120) and the backing material (110). This causes the sifting filter (120) to be firmly attached to the backing material (110). It has been found that exposure to heat at 70° C. for one minute is sufficient to cause reduction in the size of the shrink wrap (125) sufficient to tightly surround the sifting filter (120) and backing material (110). Obviously, this is not the only temperature/time combination that can be employed to reach the same result. An inlet (135) is formed through the shrink wrap (125) into the sifting filter (120). Alternatively, the shrink wrap (125) is applied in such a way that a portion of the sifting filter (120) is never covered thereby forming an inlet (135).

Figure 4A:
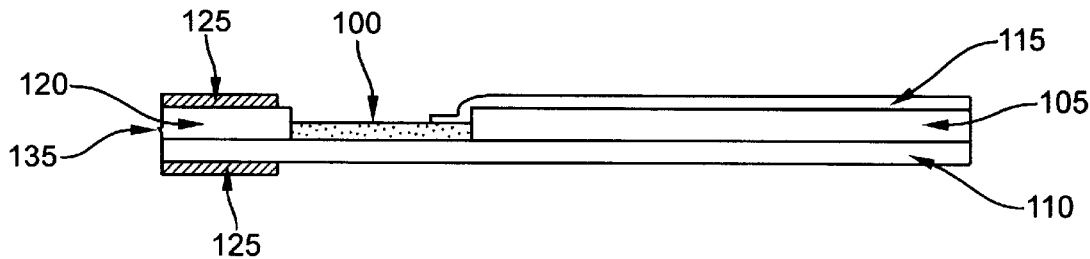
FIGS. 4A, 4B and 4C demonstrate that the shrink wrap covering of the assay device of FIG. 3 can be varied.
Figure 4B:
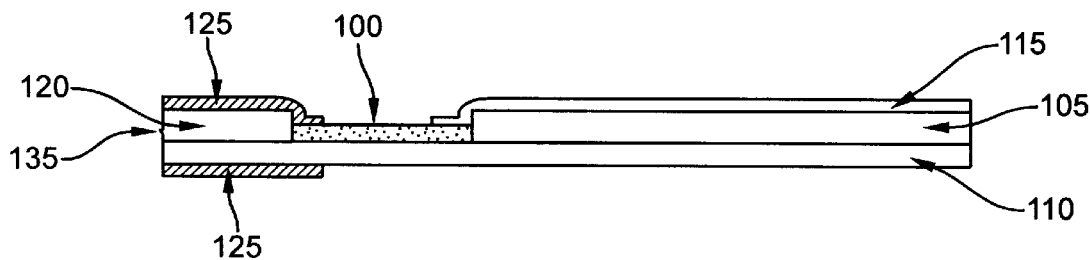
Figure 4C:
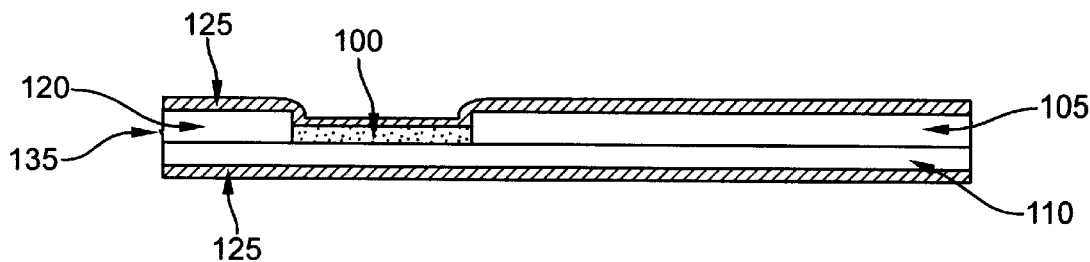

In this first inventive embodiment, the length of the shrink wrap may be customized in a number of different ways, including those shown in FIGS. 4A and 4B and 4C.

As shown in FIG. 4A, the length of the shrink wrap (125) is equal to or slightly less than the length of the sifting filter (120). In this case, the shrink wrap (125) firmly adheres the sifting filter (120) to the backing material (110) and does not contact the detection zone (100).

In FIG. 4B, the shrink wrap (125) is slightly longer than the length of the sifting filter (120). This enables the shrink wrap (125) to cover the entire sifting filter (120) and a portion of the detection zone (100). While the system of FIG. 4A is less expensive because it uses less shrink wrap (125), the system of FIG. 4B provides a test strip of higher structural integrity.

FIG. 4C shows an example where the shrink wrap (125) covers the entire test strip, thus negating any need for a covering. When applied to the test strip, the length of the shrink wrap (125) is equal to or slightly longer than the length of the test strip. When heated, as shown in FIG. 4C, the shrink wrap (125) surrounds the sifting filter (120), detection zone (100), reservoir zone (105), and backing material (110).

The placement of a sifting filter immediately preceding the detection zone, as shown in FIGS. 3, 4A, 4B and 4C, eliminates the necessity (shown in FIG. 1B and 1C) of filtering the blood in a dispenser tube. Therefore, the extra expense of a dispenser tube filter tip and a dispenser tube are eliminated. This results in a more cost effective testing system, reduces the complexity of the testing procedure, reduces the volume of the specimen and lysing solution required, and lowers the risk of cross-contamination.

Additionally, this first inventive embodiment is cheaper and easier to manufacture, handle, and store, than systems of the prior art, because expensive accessories are eliminated.

Finally, the shrink wrap used in this first embodiment not only serves as an effective structural support for the assay components, but also directs the flow of the test fluid in a manner superior to hard plastic casings due to the form fitting nature of shrink wrap. The shrink wrap controls the test fluid flow so that the test fluid only enters the device through the sifting filter inlet and, therefore, only enters the detection zone at its terminus. As shown in FIGS. 4A, 4B, and 4C, only the inlet of assay is exposed to the sample. Thus, the shrink wrap acts as a flow restrictor to channel the fluid sample into the inlet of the assay.

II. Second Inventive Assay Device

In a second inventive embodiment, the device for conducting an assay comprises: (a) a detection zone containing one inlet, wherein the detection zone comprises (i) a detection zone material that permits the passage of fluid via capillary action and (ii) a means for chemically, and/or physically, trapping and/or tagging, at least one material of interest contained in said fluid; optionally, (b) a reservoir zone aligned contiguous to the detection material, wherein the reservoir filter absorbs fluid via capillary action; optionally, (c) an underlying backing material that provides support for the detection zone and/or the sifting filter and/or the reservoir zone; (d) a casing material comprising a shrink wrap material, wherein the casing material is applied circumferentially around at least the boundary of the one inlet of the sifting material and any underlying backing in a manner that does not close the inlet; and, optionally, (e) a covering material. Preferably, the device for conducting an assay comprises: (a) said detection zone; (b) said reservoir filter; and (c) said casing material. Most preferably, the device for conducting an assay comprises: (a) said detection zone; (b) said reservoir zone; (c) said backing material; and (d) said casing material.

The materials utilized to create the detection zone, reservoir zone, backing material, casing material and covering material in this second inventive embodiment are identical to the materials utilized in the first inventive embodiment. As in the first inventive embodiment, when the analyte or material of interest is an antigen, the means for tagging and/or trapping the antigen is a homologous antibody. As in the first inventive embodiment, reagents, such a lysing reagents and additional tagging compounds (e.g. antibody coated liposomes containing dyes), can be added to the detection zone during the manufacture of the assay device. Alternatively these reagents and tagging compounds may be added immediately prior to, or immediately subsequent to, introduction of the test fluid to the assay device, by the same means used to introduce the test fluid to the assay device.

Figure 5:
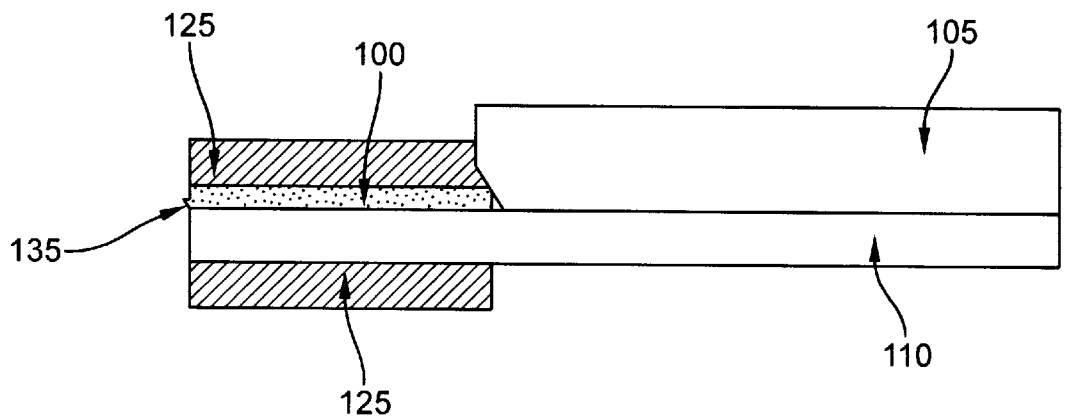
FIG. 5 illustrates a second embodiment of the present inventive assay device.

FIG. 5 is illustrative of this second embodiment. As shown in FIG. 5, a detection zone (100), which may be a nitrocellulose membrane containing attached antibodies, is positioned adjacent to a reservoir zone (105), and each zone is disposed atop a backing material (110). A covering, though not necessary and not pictured, may be used to hold the reservoir zone (105) and the detection zone (100) onto the backing material (110). A shrink wrap casing (125) is placed at least over the detection zone (100). Upon the application of heat, the shrink wrap will reduce in size and surround the detection zone (100) and backing material (110). This will cause the detection zone (100) to be firmly attached to the backing material (110). An inlet (135) is formed through the shrink wrap (125) into the detection zone (100). Alternatively, the shrink wrap (125) is applied in such a way that a portion of the detection zone (100) is never covered thereby forming an inlet (135).

Once again, this second inventive embodiment is cheaper and easier to manufacture, handle, and store, than systems of the prior art. Furthermore, in this embodiment, the shrink wrap not only serves as an effective structural support for the assay components, but also directs the flow of the sample through the inlet of the detection zone in a manner superior to hard plastic casings due to the form fitting nature of shrink wrap.

III. Third Inventive Assay Device

Figure 6A:
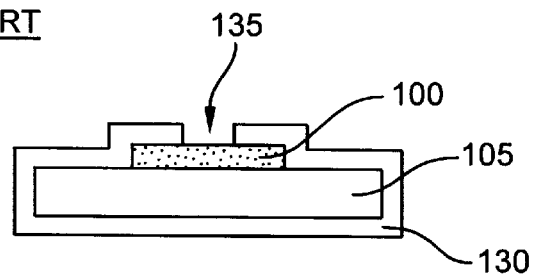
FIGS. 6A and 6B show an assay device used in the prior art.
Figure 6B:
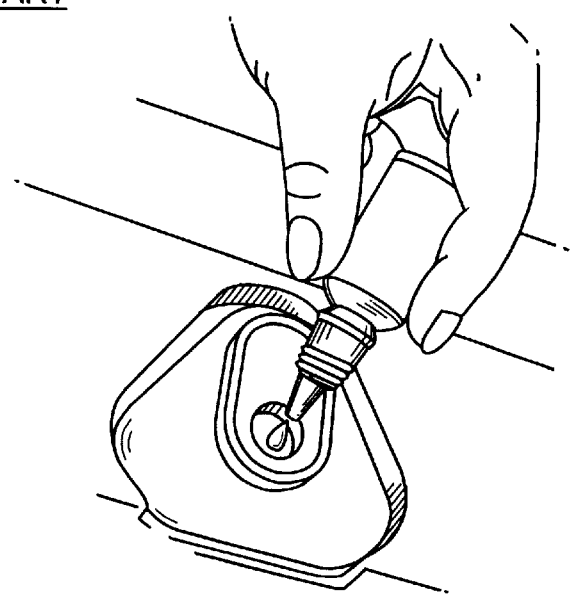

FIG. 6A shows another test strip of the prior art. As shown in FIG. 6A, a detection zone (100) is located immediately above a reservoir filter (105). A hard plastic housing (130) surrounds both the detection zone (100) and the reservoir filter (105). The hard plastic housing (130) is generally formed in two pieces that are placed around the detection zone (100) and the reservoir filter (105) and then adhered together by heat, pressure or adhesive. A preformed inlet (135) is located in the hard plastic housing (130) immediately atop the detection zone (100). By "preformed" it is meant that the inlet (135) is generally formed in the hard plastic housing (130) prior to placing the hard plastic housing (130) around the detection zone (100) and reservoir filter (105). As shown in FIG. 6B, test fluid and reagents are dropped into the assay device through the preformed inlet (135).

Applicants have developed a substantial improvement over this prior art assay that utilizes shrink wrap as an outer covering.

In this third inventive embodiment, the device for conducting an assay comprises: (a) a detection zone comprising (i) a detection zone material that permits the passage of fluid via capillary action and (ii) a means for chemically, and/or physically, trapping and/or tagging, at least one material of interest contained in said fluid; (b) a reservoir zone located immediately below the detection zone that absorbs fluid via capillary action; (c) a casing material comprising a shrink wrap material, wherein said casing completely surrounds the entire assay device; and (d) at least one inlet in the casing located immediately above the detection zone sufficient to add test fluids to the assay device.

The materials utilized to create the detection zone, reservoir zone, and casing material in this third inventive embodiment are identical to the materials utilized in the first inventive embodiment. As in the first inventive embodiment, when the material of interest is an antigen, the means for tagging, and/or trapping the antigen is a homologous antibody. As in the first inventive embodiment, reagents, such as lysing reagents and additional tagging compounds (e.g. antibody coated liposomes containing dyes), can be added to the detection zone during the manufacture of the assay device. Alternatively these reagents and tagging compounds may be added immediately prior to, or immediately subsequent to, introduction of the test fluid to the assay device by the same or a different inlet than that utilized to introduce the test fluid to the assay device.

FIGS. 7A and 7B are illustrative of this third inventive embodiment. FIGS. 7A and 7B show that the hard plastic housing (130) of the prior art device described in FIGS. 6A and 6B may be replaced with a shrink wrap casing (125).

As shown in FIG. 7A, a detection zone (100), which may be a nitrocellulose membrane containing attached antibodies, is placed immediately above a a reservoir filter (105). Both the detection zone (100) and the reservoir zone (105) are placed within a length of shrink wrap (125). The shrink wrap (125) is preferably slightly longer than the combination of the detection zone (100) and reservoir zone (105), but may be any size suitable to secure the two together.

As shown in FIG. 7B, after heating, the shrink wrap (125) closely adheres to the detection zone (100) and the reservoir zone (105). An inlet (135) is then created in the shrink wrap (125) in order to allow a sample to be deposited onto the detection zone (100). Alternatively, the inlet (135) may be preformed in the shrink wrap (125) prior to the application of heat.

This third inventive embodiment is cheaper and easier to manufacture, handle, and store, than systems of the prior art, because expensive and bulky hard plastic casings are not used.

In this embodiment, the shrink wrap not only serves as an effective structural support for the assay components, it also serves as means of directing the flow of the sample through the proper parts of the assay in a manner superior to hard plastic casings due to the form fitting nature of shrink wrap.

IV. Fourth Inventive Assay Device

Another type of prior art assay device is shown in FIG. 8. As shown in FIG. 8, a detection zone (100) is located adjacent to a reservoir filter (105). A hard plastic housing (130) surrounds the detection zone (100) and reservoir filter (105). The hard plastic housing (130) is generally formed in two pieces that are adhered together around the detection zone (100) and the reservoir filter (105) by heat, pressure or adhesive. In this prior art embodiment, the hard plastic housing (130) has numerous preformed inlets (135) which are used to introduce the fluid test sample and various reagents into the assay. By "preformed" it is meant that the inlets are generally formed in the hard plastic housing (130) prior to placing the hard plastic housing (130) around the detection zone (100) and reservoir filter (105).

Applicants have developed a substantial improvement over this prior art assay that utilizes shrink wrap as an outer covering.

In this fourth inventive embodiment, the device for conducting an assay comprises: (a) a detection zone, wherein the detection zone comprises (i) a detection zone material that permits the passage of fluid via capillary action and (ii) a means for chemically, and/or physically, trapping and/or tagging, at least one material of interest contained in said fluid; (b) an optional sifting filter, wherein the sifting filter permits the passage of fluid via capillary action, and, further, wherein the sifting filter is aligned contiguous to the detection material; optionally, (c) a reservoir zone complementing a reservoir material aligned contiguous to the detection material, and located on the side opposite the sifting filter, if present, wherein the reservoir material absorbs fluid via capillary action; optionally, (d) an underlying backing material that provides support for the detection zone and/or the sifting filter and/or the reservoir filter; (e) a casing comprising a shrink wrap material, wherein said casing completely surrounds the entire assay device; and (f) at least two inlets in the casing wherein one of the inlets is for the addition of test fluids to the assay device and the other inlet is for the addition of reagents, such as lysing reagents and tagging reagents, to the assay device. Other inlets may be present for purpose of adding additional reagents and/or increasing clarity when visually reviewing the results of the assay test. Preferably, the device also contains a reagent container that can be broken to release reagent, located in contact with the second inlet and surrounded by a shrink wrap casing, effectively affixing and sealing the reagent container and assuring that the released reagent stays sealed around the inlet when the reagent container is broken.

The materials utilized to create the detection zone, sifting filter, reservoir zone, backing material, and casing material in this fourth inventive embodiment are identical to the materials utilized in the first inventive embodiment. As in the first inventive embodiment, when the material of interest (analyte) is an antigen, the means for chemically, and/or physically, tagging, and/or trapping the antigen is a homologous antibody. As in the first inventive embodiment, reagents, such a lysing reagents and additional tagging compounds (e.g. antibody coated liposomes containing dyes), can be added to the detection zone during the manufacture of the assay device.

FIG. 9 is illustrative of this fourth inventive embodiment utilizing a reservoir filter but not a sifting filter or reagent container. In FIG. 9, a detection zone (100), which may be a nitrocellulose membrane containing bound antibodies, is located adjacent to a reservoir filter (105). Rather than utilize a hard plastic housing (130) as set forth in FIG. 8, the detection zone (100) and reservoir zone (105) are surrounded by shrink wrap (125). Inlets (135) are created in the shrink wrap casing (125) through which a fluid test sample and reagents may be added. The requisite inlets (135) may be created before or after the heating step employed to bind the shrink wrap (125) around the detection zone (100) and reservoir zone (105).

This fourth inventive embodiment is cheaper and easier to manufacture, handle, and store, than systems of the prior art, because expensive and bulky hard plastic casings are not used.

In this embodiment, shrink wrap not only serves as an effective structural support for the assay components, but also directs the flow of the sample through the inlet of the assay device in a manner superior to hard plastic casings due to the form fitting nature of shrink wrap.

The shrink wrap enclosed reagent container provides a more consolidated, effective, safe, and contaminate free method for adding reagent to the assay device.

With regard to all of the inventive assay device embodiments set forth in this application, it must be stressed that although the assay devices are primarily geared toward detecting and identifying infection causing antigens in bodily fluids, this is not the only use for said devices. The assay devices are capable of detecting and identifying any material of interest (analyte) in any biological and/or industrial fluid, as long as the detection material contains a binder, or means of trapping and/or tagging the material of interest. The nature of the binder, or means of trapping and/or tagging the material of interest will naturally vary according to the nature of the material of interest and are readily ascertainable by those of ordinary skill in the art. In example, if the material of interest is a DNA, the means of trapping and/or tagging the material of interest is a complementary DNA and if the material of interest is a PNA, the means for trapping and/or tagging the material of interest is a complementary PNA. An infinite number of compounds can be detected in biological and/or industrial fluids utilizing the inventive assays, including, but not limited to, analytes, antigens, polynucleotides, oligonucleotides, small molecules, drugs of abuse, therapeutic drugs, carbohydrates, environmental and carcinogenic agents, parasites, bacteria, viruses, and prions.

The foregoing descriptions of the present invention have been presented for the purposes of illustration and description but are not intended to represent the full limits of the invention. Minor variations and modifications within the skill of those of ordinary skill in the relevant art are also considered to be within the scope of the present invention. Therefore, the appended claims should be construed in a manner that includes alternative embodiments to the extent permitted by law.

I hereby claim the following:

1. A device for conducting an assay for an analyte of interest in a fluid comprising:
   a) a sifting filter containing one inlet having boundaries, wherein said inlet is capable of having said fluid applied through said inlet to said sifting filter, and said sifting filter permits passage of said fluid through said sifting filter by capillary action, and further wherein said sifting filter is aligned contiguous to a detection zone in said device;
   b) the detection zone, comprising
      (i) a detection zone material which permits passage of fluid from the sifting filter through said detection zone material by capillary action, and
      (ii) a binder for said analyte; and
   c) a casing material for structural support of at least one element of the device and for directing passage of fluid in the device, said casing material comprising a shrink wrap material, wherein the casing material covers at least a portion of the sifting filter and covers circumferentially at least the boundaries of said inlet of the sifting filter.

2. The device of claim 1, further comprising:
   d) an underlying backing material that provides support for the sifting filter and the detection zone.

3. The device of claim 2, further comprising:
   e) a covering material for attaching the detection zone to the backing material.

4. The device of claim 2, wherein said fluid is a bodily fluid, said analyte is an antigen, and said binder is a monologous antibody specific to said antigen.

5. The device of claim 3, wherein said fluid is a bodily fluid, said analyte is an antigen, and said binder is a monologous antibody specific to said antigen.

6. The device of claim 1, further comprising:
   d) a reservoir zone aligned contiguous to the detection zone and located on the side of the device opposite the sifting filter, wherein the reservoir zone comprises a reservoir material which permits remaining fluid in the detection zone to be absorbed by capillary action into the reservoir material.

7. The device of claim 6, further comprising:
   e) an underlying backing material that provides support for the sifting filter, the detection zone and the reservoir zone.

8. The device of claim 7, further comprising:
   f) a covering material for attaching the detection zone to the backing material.

9. The device of claim 8, wherein said fluid is a bodily fluid, said analyte is an antigen, and said binder is a homologous antibody specific to said antigen.

10. The device of claim 6, wherein said fluid is a bodily fluid, said analyte is an antigen, and said binder is a homologous antibody specific to said antigen.

11. The device of claim 7, wherein said fluid is a bodily fluid, said analyte is an antigen, and said binder is a homologous antibody specific to said antigen.

12. The device of claim 7, wherein said casing material is further circumferentially around any underlying backing material in a manner that does not close the inlet and further wherein said casing material covers all of the length of the sifting filter and all of the length of the underlying material supporting the sifting filter.

13. The device of claim 7, wherein said casing material is further circumferentially around any underlying backing material that does not close the inlet and further wherein said casing material covers at least a portion of the underlying backing material supporting the sifting filter.

14. The device of claim 7, wherein said casing material is further circumferentially around any underlying backing material that does not close the inlet and further wherein said casing material covers the entire sifting filter and underlying backing material supporting the sifting filter and at least a portion of the detection zone and underlying backing material supporting the detection zone.

15. The device of claim 7, wherein said casing material is further circumferentially around any underlying backing material that does not close the inlet and further wherein said casing material covers the entire device and the entire underlying backing material.

16. The device of claim 2, wherein said fluid is a bodily fluid, said analyte is an antigen, and said binder is a homologous antibody specific to said antigen.

17. A device for conducting an assay for an analyte of interest in a fluid comprising:
   a) a detection zone, comprising:
      (i) a detection zone material which permits passage of fluid through said detection zone material by capillary action, (ii) a binder for said analyte; and (iii) one inlet having boundaries;

b) a casing material for structural support of at least one element of the device and for directing passage of fluid in the device, said casing material comprising a shrink wrap material, wherein said casing material surrounds circumferentially at least the boundaries of the inlet of the detection zone and at least a portion of the detection zone.

18. The device of claim 17, further comprising:

c) an underlying backing material that provides support for the detection zone.

19. The device of claim 18, further comprising:

d) a covering material for attaching the detection zone to the backing material.

20. The device of claim 18, wherein said fluid is a bodily fluid, said analyte is an antigen, and said binder is a homologous antibody specific to said antigen.

21. The device of claim 19, wherein said fluid is a bodily fluid, said analyte is an antigen, and said binder is a homologous antibody specific to said antigen.

22. The device of claim 17, further comprising:

c) a reservoir zone aligned contiguous to the detection zone, wherein the reservoir zone comprises a reservoir material which permits remaining fluid in the detection zone to be absorbed by capillary action into the reservoir material.

23. The device of claim 22 further comprising:

d) an underlying backing material that provides support for the detection zone and the reservoir zone.

24. The device of claim 23, further comprising:

e) a covering material for attaching the detection zone to the backing material.

25. The device of claim 24, wherein said fluid is a bodily fluid, said analyte is an antigen, and said binder is a homologous antibody specific to said antigen.

26. The device of claim 22, wherein said fluid is a bodily fluid, said analyte is an antigen, and said binder is a homologous antibody specific to said antigen.

27. The device of claim 23, wherein said fluid is a bodily fluid, said analyte is an antigen, and said binder is a homologous antibody specific to said antigen.

28. The device of claim 23 wherein said casing material covers at least a portion of the underlying material supporting the detection zone.

29. The device of claim 23, wherein said casing material covers the entire device and the entire underlying backing material.

30. The device of claim 17, wherein said fluid is a bodily fluid, said analyte is an antigen, and said binder is a homologous antibody specific to said antigen.

31. A device for conducting an assay for an analyte of interest in a fluid comprising:

a) a detection zone, comprising:

(i) a detection zone material which permits passage of fluid through said detection zone material by capillary action; and (ii) a binder for said analyte;

b) a reservoir zone aligned contiguous to the detection zone, said reservoir zone comprising a reservoir material which permits remaining fluid in the detection zone to be absorbed by capillary action into the reservoir material; and c) a casing material for structural support of at least one element of the device and for directing passage of fluid in the device, said casing material comprising a shrink wrap material, wherein said casing material completely surrounds the entire device and further wherein said casing material has at least one inlet located immediately above the detection zone wherein said inlet is capable of having said fluid applied through said inlet to the device detection zone.

32. The device of claim 31 wherein said fluid is a bodily fluid, said analyte is an antigen, and said binder is a homologous antibody specific to said antigen.

* * * * *